United States Patent [19]

Marcuse et al.

[11] Patent Number: 4,492,463
[45] Date of Patent: Jan. 8, 1985

[54] METHOD FOR INSPECTING MULTILAYER TRANSPARENT RODS

[75] Inventors: Dietrich Marcuse, Lincroft; Herman M. Presby, Highland Park, both of N.J.

[73] Assignee: AT&T Bell Laboratories, Murray Hill, N.J.

[21] Appl. No.: 362,961

[22] Filed: Mar. 29, 1982

[51] Int. Cl.³ ............................................. G01N 21/88
[52] U.S. Cl. ..................... 356/73.1; 356/239
[58] Field of Search ............... 356/73.1, 128, 239

[56] References Cited

U.S. PATENT DOCUMENTS

| 3,777,171 | 12/1973 | Hollenbeck | 356/239 X |
| 4,161,656 | 7/1979 | Marcuse et al. | 250/459 |
| 4,168,907 | 9/1979 | Presby | 356/73.1 |
| 4,181,433 | 1/1980 | Marcuse | 356/73.1 |
| 4,307,296 | 12/1981 | Presby | 356/73.1 X |

OTHER PUBLICATIONS

"Optical Fiber Preform Diagnostics", Presby et al., Applied Optics, vol. 18, No. 1, Jan. 1, 1979, pp. 23-30.

*Primary Examiner*—Vincent P. McGraw
*Attorney, Agent, or Firm*—Sylvan Sherman; Bernard Tiegerman

[57] ABSTRACT

Various techniques for examining the core region of optical fibers and fiber preforms involve placing a portion of the fiber/preform in an index-matching fluid and transversely illuminating the immersed portion. As described herein, the use of an index-matching fluid can be eliminated by illuminating the fiber/preform with a diverging beam. By the suitable selection of parameters, refraction at the air-fiber/preform interface can produce a well colliminated beam within the core region.

4 Claims, 8 Drawing Figures

METHOD FOR INSPECTING MULTILAYER TRANSPARENT RODS

TECHNICAL FIELD

This invention relates to methods for examining the internal structure of optical fibers and fiber preforms.

BACKGROUND OF THE INVENTION

Techniques for quantitatively evaluating the internal structure of optical fibers and fiber preforms are described in U.S. Pat. Nos. 4,161,656 and 4,181,433. Because these techniques, and the one to be described hereinbelow are equally applicable to both optical fibers and fiber preforms, either term or the term "fiber/preform" will be used hereinafter to designate both.

In the '656 patent, the fluorescence induced in the index-modifying dopants used to grade the index profile is measured. Alternatively the absorption by the dopants of the fluorescence-inducing ultraviolet (uv) is measured. In the '433 patent, the density distribution of the incident light as, focused by the fiber/preform core region, is measured. For accurate results, both of these techniques require that the radiation incident upon the core of the fiber/preform be a well collimated, uniform wave. However, because of the strong focusing action of the surrounding cladding it was deemed necessary to immerse the fiber/preform in an indexing-matching fluid in order to maintain the planar nature of the illuminating beam, and to observe the entire core region. Without such immersion, the strong focusing action of the cladding makes it virtually impossible for an observing lens of reasonable size to collect the sharply diverging rays that traverse the core.

Another problem associated with the use of matching fluids is the nonavailability of conveniently usable, low-loss fluids having high indices (i.e., >1.6). The problem is that the heavier fluids, having the requisite high indices, tend to be toxic and therefore more difficult to handle. Finally, even when the required matching fluids are available, their use is not only an inconvenience, but there is always the possibility of scratching the preform and damaging it when it is being wiped clean of the fluid. Advantageously, measuring techniques which avoid the use of matching fluids are preferable.

SUMMARY OF THE INVENTION

In accordance with the present invention, the need for index-matching fluids in the measurement of fiber/preforms is eliminated by illuminating the fiber/preform with a diverging beam. This, in conjunction with the strong focusing action of the fiber/preform cladding, can be made to produce a well collimated, plane wave at the fiber/preform core. Thus the core region is readily observable and the planar nature of the beam allows for accurate profile results.

In accordance with one embodiment of the invention, the required diverging beam is produced by a rod-lens made of the same material as the fiber/preform that is to be measured. More generally, any means for providing the diverging beam can be employed.

DETAILED DESCRIPTION

Figure 1:
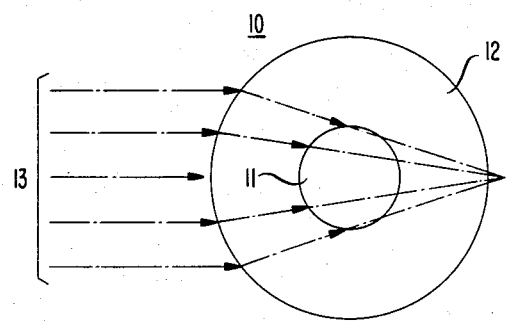
FIG. 1 shows a cross section of a typical optical fiber preform and the focusing effect produced on a transversely directed light beam.

Referring to the drawings, FIG. 1 shows a cross section of an optical fiber preform 10 comprising an inner core region 11 surrounded by an outer cladding 12 of lower refractive index material. (Some preforms are made with two or more claddings. However, for the purpose of explaining the present invention, a single-clad preform is illustrated.) The core can be made of a homogeneous material having a constant refractive index, or it can be fabricated by depositing a plurality of layers of materials of the same or different refractive indices to produce either a step or a graded index preform.

Whatever process is used to fabricate the preform, the fiber that can be drawn from it will be no better than the preform itself. Accordingly, it is essential that the preform be inspected before the fiber is drawn to determine its internal structure. This can be done in a variety of ways, as explained in the above-identified patents. Typically, the maximum difference in the refractive indices of the core and cladding is only a few hundreds of a percent and, as such, refraction at the core-cladding interface is very small. However, there can be a considerable difference between the indices of the cladding and the surrounding ambient, such as air. For silica preforms, the cladding index is 1.46. As such, there is a significant refraction produced at the air-cladding interface. This is illustrated in FIG. 1 which shows the effect the cladding has on the parallel rays 13 associated with a planar wave incident upon preform 10. As can be seen, the incident rays are refracted at the air-cladding interface and, as a result, are incident upon the core as a strongly converging beam. As indicated above, this is unsatisfactory for making accurate measurements of the core profile.

Figure 2:
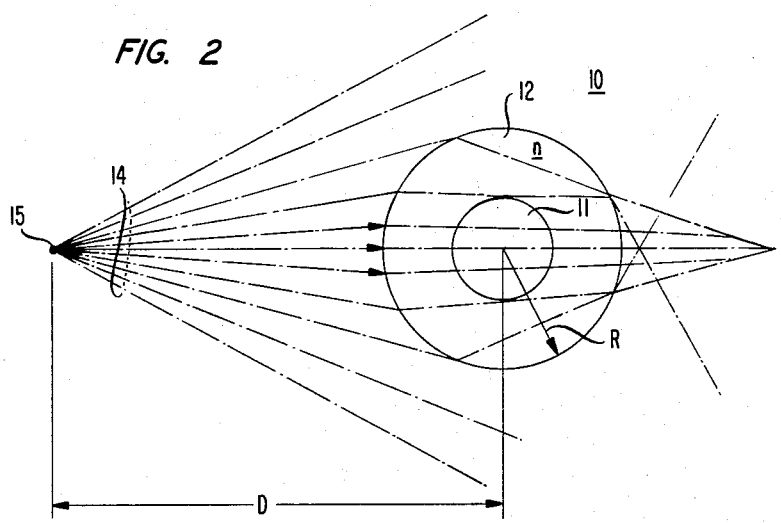
FIG. 2 shows the effect produced upon a diverging light beam by the preform of FIG. 1.

Ordinarily, index matching fluid is used to avoid light refraction at the outer preform boundary. In an alternative arrangement, in accordance with the present invention, a diverging beam is used to illuminate the preform, as shown in FIG. 2. Using the same identification numerals as in FIG. 1 to identify corresponding portions of preform 10, FIG. 2 shows a group of diverging rays 14 incident upon preform 10. In this embodiment, the refraction at the air-cladding interface bends the rays so that the paraxial rays are parallel within the core region. For a preform of radius R, and a refractive index n, such parallel rays are produced when the equivalent point source 15 is located a distance D from the preform center given by $$D = \frac{n}{n-1} \cdot R \tag{1}$$

Figure 3:
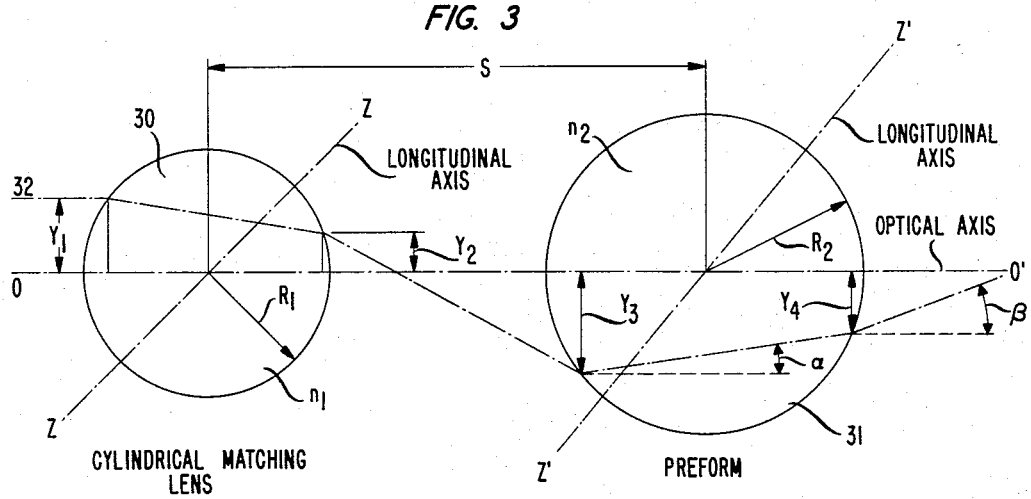
FIG. 3, included for purposes of explanation, shows the path of an arbitrary light ray as it traverses a circular cylindrical matching lens and a preform.

The equivalent of such a point source is conveniently obtained by means of a matching circuit-cylindrical rod-lens whose longitudinally axis z—z is aligned parallel to the longitudinal axis z'—z' of the preform at a distance S, as illustrated in FIG. 3. Designating the radii and indices of the lens 30 and preform 31 as $R_1$, $n_1$ and $R_2$, $n_2$, respectively, the angle $\alpha$ of an incident ray 32 within the preform is given by $$\alpha = \frac{Y_1}{R_1 R_2}\left[2S\frac{(n_1-1)(n_2-1)}{n_1 n_2} - R_1\frac{n_2-1}{n_2} - 2R_2\frac{n_1-1}{n_1}\right] \quad (2)$$

where $Y_1$ is the distance between one of incident parallel rays and the plane defined by axes z—z and z'—z'.

For the rays to be collimated within the preform, $\alpha$ is made equal to zero and we obtain $$S = \frac{n_1 R_1 (n_2-1) + 2n_2 R_2 (n_1-1)}{2(n_1-1)(n_2-1)}. \quad (3)$$

For the special case where the lens and preform are made of the same material ($n_1 = n_2 = n$) equation (3) reduces to $$S = \frac{n(R_1 + 2R_2)}{2(n-1)}. \quad (4)$$

If, in addition, the lens and preform have the same radius, $R_1 = R_1 = R$, we obtain $$S = \frac{3R}{2}\left(\frac{n}{n-1}\right). \quad (5)$$

Figure 4:
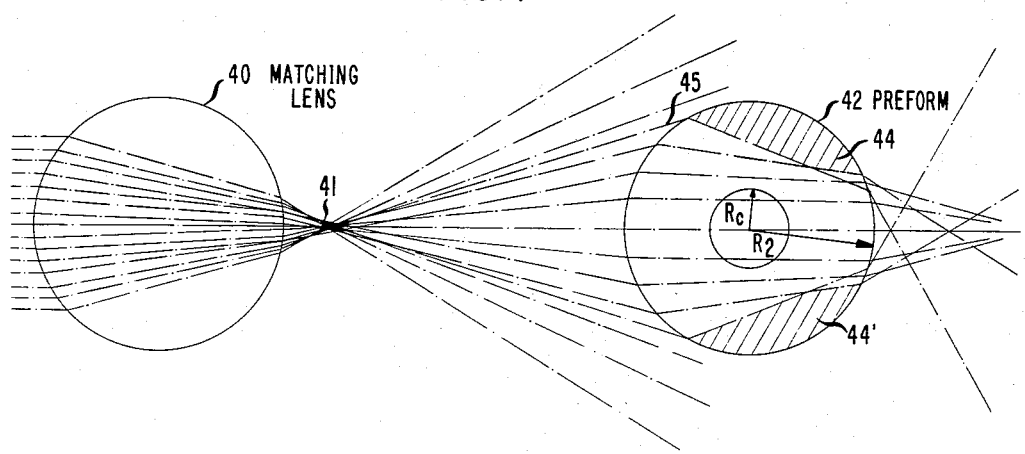
FIGS. 4-8 show various arrangements of matching lenses and preforms.

Unfortunately, a circular lens is not a very good lens in the sense that it does not have a single, well defined focal point. This is illustrated in FIG. 4 which shows the focusing effect of a matching lens 40 upon an incident beam. As can be seen, the converging rays do not intersect at a single point but, instead, intersect over an interval 41. In addition, there are portions 44 and 44' of the preform 42 that are inaccessible to the incident rays and, hence, cannot be viewed by this technique. To see why, consider a ray 45 which is tangent to the preform. Whereas rays at a smaller angle of incidence can enter the preform, rays at a larger angle cannot. Hence, the shaded regions 44 and 44' remain unilluminated. Moreover, rays incident at these relatively large angles of incidence do not traverse the preform at an angle $\alpha = 0$. For these reasons, it is advantageous to restrict the use of this technique to preforms and fibers having a core radius $r_c$ that is small relative to the outer cladding radius $R_2$. A practical limit is given by $$r_c < \frac{R_2}{2}. \quad (6)$$

Within this region, near the preform axis, the beam is well collimated and the core is well removed from the shaded regions.

EXAMPLES

FIGS. 5 to 8 show ray tracings computed for matching lenses and preforms having different relative sizes and spacings. In all cases the indices $n_1$ and $n_2$ are the same and equal to 1.46.

Figure 5:
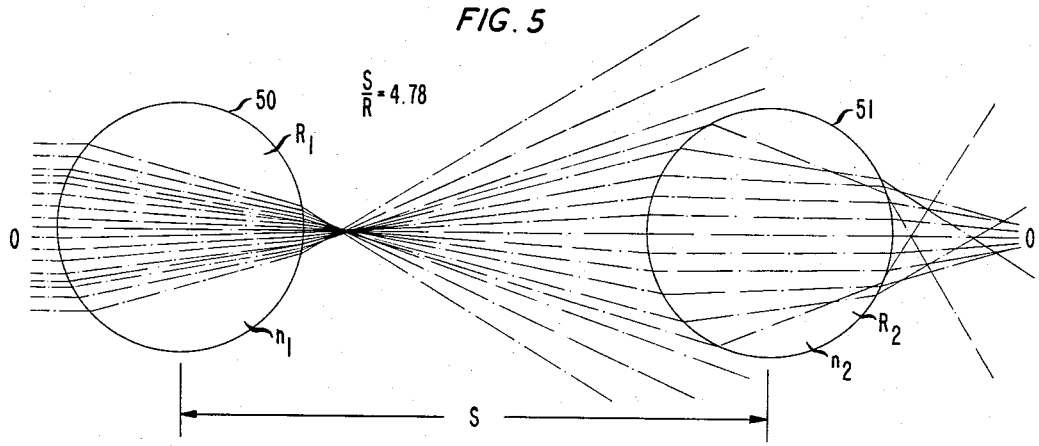
Figure 6:
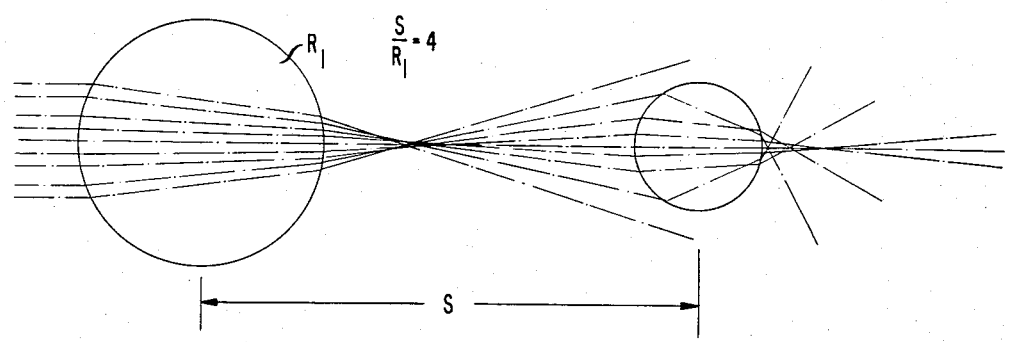
Figure 7:
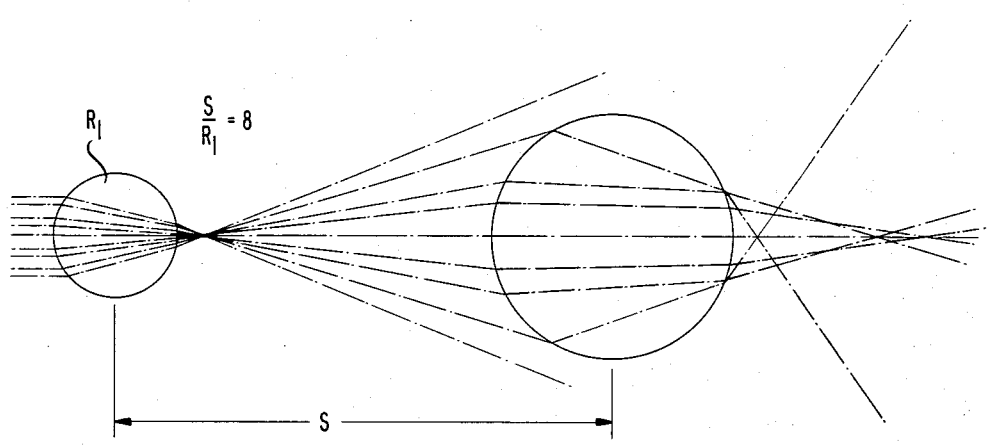

In the example of FIG. 5 the radii $R_1 = R_2 = R$, and the spacing S is such that $S/R = 4.78$. For this case the rays near the optical axis 0—0 are seen to be well collimated in the preform. This condition can also be obtained for the cases where the lens radius is larger or smaller than the preform radius, as shown in FIGS. 6 and 7.

Figure 8:
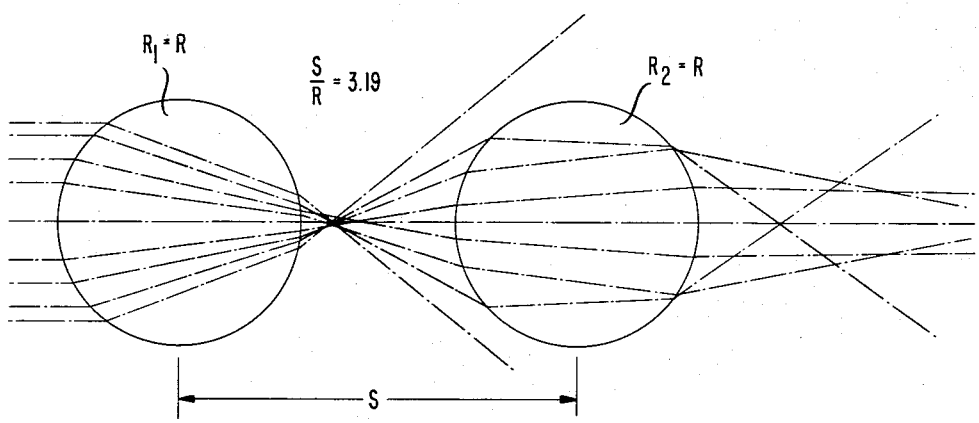

FIG. 8, by contrast, shows a less satisfactory choice of parameters leading to a condition of slightly diverging rays within the preform.

These several examples illustrate the variety of lens sizes and spacings that can be employed to achieve a well collimated light beam within the preform in accordance with the invention.

While a simple rod-lens was used to demonstrate the principles of the present invention, it will be recognized that other lens structures can just as readily be employed. The principle advantages of the rod-lens are its simplicity and easy availability.

What is claimed is:

1. A method for fabricating an optical fiber, comprising the steps of:
    forming an optical fiber which includes a longitudinal axis and a surface;
    impinging at least a characteristic region of said fiber with electromagnetic radiation while said region is immersed in a fluid medium, said fluid medium and said region being at least partially transparent to said radiation, and the index of refraction of said fluid medium being different from that of said region;
    detecting electromagnetic radiation emanating from said region; and
    accepting the whole of said fiber if the structure of said region, as determined from the detected radiation, conforms to a desired standard,
    characterized in that
    at least a portion of said impinging electromagnetic radiation is a diverging beam of light lying in a plane transverse to said longitudinal axis, said beam undergoing refraction at said surface, and the divergence of the beam being chosen so that after said refraction, at least a portion of the beam is substantially collimated.

2. The method according to claim 1 wherein said diverging beam is produced by a rod lens.

3. A method for fabricating an optical fiber, comprising the steps of:
    forming an optical fiber preform which includes a longitudinal axis and a surface;
    impinging, during or subsequent to said forming step, at least a characteristic region of said preform with electromagnetic radiation while said region is immersed in a fluid medium, said fluid medium and said region being at least partially transparent to said radiation, and the index of refraction of said fluid medium being different from that of said region;
    detecting at least a portion of the electromagnetic radiation emanating from said region;
    accepting the whole of said preform if the structure of said region, as determined from the detected radiation, conforms to a desired standard; and
    further processing said accepted preform to form said optical fiber,
    characterized in that
    at least a portion of said impinging electromagnetic radiation is a diverging beam of light lying in a plane transverse to said longitudinal axis, said beam undergoing refraction at said surface, and the divergence of the beam being chosen so that after said refraction, at least a portion of the beam is substantially collimated.

4. The method according to claim 3 wherein said diverging beam is produced by a rod lens.

* * * * *